United States Patent
Wright

(10) Patent No.: US 6,911,438 B2
(45) Date of Patent: Jun. 28, 2005

(54) HORMONE REPLACEMENT FORMULATION

(76) Inventor: Jonathan V. Wright, 36638 32nd S., Auburn, WA (US) 98001

( * ) Notice: Subject to any disclaimer, the term of this patent is extended or adjusted under 35 U.S.C. 154(b) by 0 days.

(21) Appl. No.: 09/951,489

(22) Filed: Sep. 12, 2001

(65) Prior Publication Data

US 2003/0050287 A1 Mar. 13, 2003

(51) Int. Cl.⁷ .............................................. A61K 31/56
(52) U.S. Cl. ........................ 514/170; 514/171; 514/179; 514/182
(58) Field of Search ................................ 514/170, 171, 514/182, 179

(56) References Cited

U.S. PATENT DOCUMENTS

| | | | |
|---|---|---|---|
| 6,174,665 B1 * | 1/2001 | Dullien ........................... | 435/4 |
| 6,329,358 B1 * | 12/2001 | Cavazza ...................... | 514/171 |
| 6,479,545 B1 * | 11/2002 | Levinson et al. ........... | 514/560 |

FOREIGN PATENT DOCUMENTS

| | | | | |
|---|---|---|---|---|
| JP | 403115222 A | * | 5/1991 | ......... A61K/31/565 |
| JP | 403115222 | * | 5/1991 | ......... A61K/31/565 |
| WO | WO99/53910 | * | 10/1999 | .......... A61K/31/00 |

OTHER PUBLICATIONS

JP 403115222, Derwent Abstract, Derwent –ACC–No. 1991–188847.*

"Textbook of Organic Medicinal and Pharmaceutical Chemistry", Dwight S. Fullerton et al., 9th edition (Jan. 1991) Lippincott Williams & Wilkins Publishers, p. 691, 694, 698.*

Schubert et al., "Hormonsubstitution in der Postmenopause–Auswirkungen auf Spurenelemente und ox. LDL–Antikorper (Substituttion of hormones in the post–menopause effects on trace elements and ox. LDL antibodies)", 1996, Mengen– Spurenelem, p. 57–63.*

CAPLUS abstract, Accession No. 1997:421726, 1996, Schubert et al., p. 1.*

* cited by examiner

*Primary Examiner*—Shengjun Wang
(74) *Attorney, Agent, or Firm*—Jensen & Puntigam PS

(57) ABSTRACT

The formulation comprises a combination of three estrogens and selected amount of other elements. The three estrogens include 2-hydroxyestrone, 17-beta estradiol, and estriol. The amount of 17-beta estradiol is substantially less than the amounts of 2-hydroxyestrone and estriol, both which are approximately equal in amount. The amounts of pyridoxine, folic acid, selenium and cobalt are therapeutically effective amounts.

7 Claims, No Drawings

HORMONE REPLACEMENT FORMULATION

TECHNICAL FIELD

This invention relates generally to hormone replacement therapy, and more specifically concerns a new estrogen replacement formulation.

BACKGROUND OF THE INVENTION

Hormone replacement therapy has been known for some time. One particular aspect of hormone replacement therapy, known generally as estrogen replacement, has been used for over 30 years for women during or following menopause. The reason for estrogen replacement, which is usually accomplished through transdermal absorption or orally, is to make up for the decline in, or the low level of, estrogen produced by the body. Typically, estrogen production decreases and then declines dramatically during and after menopause. It is during this time period that estrogen replacement is normally prescribed by a physician. However, estrogen replacement can be prescribed in other circumstances where other causes account for a decline in estrogen production or if estrogen is produced at a lower than desirable level. This could occur in women not yet in menopause.

The reasons for estrogen replacement, which have been substantiated by scientific research over a number of years, include the prevention and/or treatment of osteoporosis and cardiovascular disease, as well as preventing age-related decline in mental function. Estrogen replacement has also been used to decrease age-related changes in appearance.

The most commonly prescribed estrogen for estrogen replacement is actually concentrated from horse urine, referred to generally as equine-conjugated estrogen or just equine estrogen. In addition, a single naturally occurring human estrogen metabolite, typically 17-beta estradiol, in the form of a "patch", has also been and is currently prescribed. Many physicians and others have objected to equine estrogen as being inappropriate for human use and even possibly dangerous because of the fact that many individual horse estrogens are not present in human bodies and, hence, there is a lack of correlation between equine estrogen and the human estrogen which is to be replaced. There is also some evidence of the carcinogenic effect of equine estrogen.

As indicated above, the use of natural 17-beta estradiol (a single estrogen) typically occurs in the form of an estrogen patch. While clearly more appropriate for estrogen replacement than equine estrogen, this single estrogen is believed to be incomplete for estrogen therapy, because of the large number of different estrogens and their metabolites which normally circulate in the blood stream of human bodies, particularly in women.

In this regard, several specific human estrogens, sometimes referred to as "classical" human estrogens, have been the subject of extensive research in replacement therapy. These classical estrogens include estrone, estradiol (17-beta estradiol) and estriol. Estriol has been found to be relatively weak in its therapeutic benefits, while 17-beta estradiol is considered the most potent, but is generally agreed to be slightly carcinogenic. Estrone also has a carcinogenic effect, although both estrone and 17-beta estradiol are less carcinogenic than equine estrogens. There is disagreement with respect to the carcinogenic effect of estriol, ranging from non-carcinogenic or even anti-carcinogenic to slightly carcinogenic.

In an attempt to duplicate or mimic the presence of natural estrogens in the human body by replacement therapy, some physicians in the 1980s began to prescribe combinations of the three classical human estrogens, namely, a combination of estrone, 17-beta estradiol and estriol. Typically, the combination has been 80% estriol, 10% estrone and 10% estradiol, although these percentages have varied somewhat from formulation to formulation.

However, even with natural estrogen replacement, there is still concern relative to its carcinogenic effect as well as other undesirable possibilities. Given the fact that estrogen replacement has been documented to have considerable health benefits, it is certainly desirable to develop an estrogen replacement formulation which is not only appropriate, natural and effective, but also is designed to prevent or minimize negative side effects, including carcinogenic side effects.

DISCLOSURE OF THE INVENTION

Accordingly, the present invention is an estrogen formulation for use in hormone replacement therapy, comprising: a combination of two estrogens, including 2-hydroxyestrone and 17-beta estradiol, wherein the amount of 17-beta estradiol is substantially less than the amount of 2-hydroxyestrone.

BEST MODE FOR CARRYING OUT THE INVENTION

As indicated above, both historically and still to a significant extent today, equine estrogen, made from horse urine, is used for human estrogen replacement therapy. However, advantages in using natural estrogen have led many physicians to prescribe a particular single naturally occurring estrogen metabolite, e.g. 17-beta estradiol, or more recently a formulation of three "classical" estrogens, namely, estrone, 17-beta estradiol and estriol.

Ongoing research, however, has revealed that there are many estrogens present in the human body. These additional estrogens include principally, but are not limited to estrone, 2-hydroxyestrone, 2-methoxyestrone, 4-hydroxyestrone, 15-alpha-hydroxyestrone, 16-alpha-hydroxyestrone, 16-beta-hydroxyestrone, estradiol (17-beta estradiol), 2-hydroxy-estradiol, 2-methoxy-estradiol, 4-hydroxy-estradiol, 16-oxoestradiol, estriol, 16-epiestriol and 17-epiestriol. This is not intended to be an exhaustive list, as there are still other estrogens and their metabolites which are present in the human body. However, it does include what is presently believed to be most of the estrogens present under normal circumstances.

The present invention, in its preferred embodiment, is a new formulation involving several estrogens which are normally circulating in the human body in combination with a number of other elements which are designed to complement and work in conjunction with the selected estrogens to enhance and increase their therapeutic effect, as well as reducing their anti-therapeutic effects/disadvantages.

The new formulation is based on the estrogen levels in the blood as opposed to estrogen levels in the urine and is therefore more closely aligned with the way actual estrogens are present and at work in the body. The two most abundant estrogens present in the blood stream are estriol and 2-hydroxyestrone, in approximately equal amounts. 17-beta estradiol was included in the present formulation, since it is the most therapeutically effective. 2-hydroxyestrone has been shown to be protective against cancer, while estriol is either non-carcinogenic or perhaps even slightly anti-carcinogenic. 17-beta estradiol has been indicated to be somewhat carcinogenic, and hence the quantity of this ingredient is severely limited. In the present formulation, for the three estrogens, 2-hydroxyestrone and the estriol are approximately in the range of 38–44% by weight, while the 17-beta-estradiol can vary between 10–20% by weight. In an embodiment which includes just 2-hydroxyestrone and 17-beta estradiol, the formulation is 80–90% of 2-hydroxyestrone and 10–20% of 17-beta estradiol. From the extremely large number of possible estrogen combinations, the above combinations have been discovered to be quite effective.

More particularly with respect to the three estrogen formulation, the 17-beta estradiol, while the smallest in quantity, is generally believed to be the most potent of all the estrogens and provides the greatest therapeutic effect, but also provides the greatest carcinogenic risk. The 2-hydroxyestrone is associated with lower degrees of cancer risk, particularly in high amounts. 2-hydroxyestrone is sometimes referred to as "good estrogen". It is, however, considered a weak estrogen, with only a mild degree of estrogen-protective activity. However, the non-carcinogenic weak estrogen can help to protect against estrogen-related cancer by occupying selected receptor sites that might otherwise be stimulated by the more carcinogenic 17-beta estradiol. 2-hydroxyestrone has been found to be the first or second most abundant estrogen in the human blood stream.

Estriol, while another weak estrogen, is generally regarded to be anti-carcinogenic or neutral. It also protects against carcinogenic estrogens by occupying receptor sites and is a detoxification product of the various other estrogens. Further, estriol is also either the first or second most abundant of the natural estrogens in the blood stream.

The above three estrogens, in the general quantities disclosed, are a new and therapeutically effective combination of estrogens, while minimizing any resulting cancer possibilities.

The present formulation in its preferred form includes several additional elements. One element is pyridoxine (Vitamin B6). The additional of pyridoxine is designed to help depression and fluid retention which sometimes results from estrogen interfering with various enzyme systems which depend upon pyridoxine for proper functioning.

A second additional element is folic acid, which has often been found to be low in postmenopausal women, and has also been found to be important for maintaining normal brain function. Estrogen replacement can interfere with natural folic acid metabolism.

Another additional element is selenium, which reduces the risk of breast cancer. Lastly, cobalt has been found to be helpful, since without sufficient cobalt, the effect of estrogen replacement therapy can be significantly reduced, if not eliminated. The addition of cobalt prevents the enzymes from clearing the replacement estrogen from the body too rapidly, which helps to maintain the effectiveness of the estrogen replacement therapy regimen.

The quantities of pyridoxine and the other elements can certainly vary, as long as sufficient amounts are provided for a normal therapeutic effect. Generally, however, where the 2-hydroxyestrone and the estriol are in the range of 1000–2500 micrograms, although a preferred range is 1000–1125 micrograms, pyridoxine will be approximately 20 milligrams, with folic acid being in the range of 400–800 micrograms and selenium and cobalt in the range of 200–300 micrograms. Each of these elements ensure an effective level of the ingredients.

The above-described formulation provides not only the significant benefits of estrogen replacement in a natural form, but also includes other elements which are specifically designed to reduce or eliminate certain problems or disadvantages potentially caused by replacement estrogen, or as a side effect thereof. Hence, the present formulation is an effective but safe hormone treatment, maintaining the advantages of estrogen replacement without the previous disadvantages.

Although a preferred embodiment of the invention has been disclosed here for purposes of illustration, it should be understood that various changes, modifications and substitutions may be incorporated without departing from the spirit of the invention, which is defined by the claims which follow. In particular, the amounts of the various elements can be varied somewhat, as long as the therapeutic effect described is maintained.

What is claimed is:

1. An estrogen formulation for use in hormone replacement therapy, comprising:
 a combination of three estrogens, the combination including an amount of 2-hydroxyestrone, an amount of 17-beta estradiol, and an amount of estriol, wherein the amounts of 2-hydroxyestrone and estriol are approximately equal and wherein each comprise approximately 35%–45% by weight of the three estrogens, and wherein the 17-beta estradiol comprises the remainder of the three estrogen combination.

2. A formulation of claim 1, further including a selected amount of cobalt.

3. A formulation of claim 1, further including a selected amount of selenium.

4. a formulation of claim 2, further including a selected amount of selenium.

5. A formulation of claim 4, further including selected amounts of pyridoxine and folic acid.

6. An article of claim 5, wherein the formulation comprises 1000–1125 micrograms of 2-hydroxyestrone, 200–500 micrograms of 17-beta-estradiol, 1000–1125 micrograms of estriol, 20 milligrams of pyridoxine, 400–800 micrograms of folic acid; 200–300 micrograms of cobalt; and 200–300 micrograms of selenium.

7. An estrogen formulation for use in hormone replacement therapy, comprising:
 a combination of two estrogens, the combination including an amount of 2-hydroxyestrone and an amount of 17-beta estradiol, wherein the formulation comprises 80–90% of 2-hydroxyestrone and 10–20% of 17-beta estradiol.

* * * * *

UNITED STATES PATENT AND TRADEMARK OFFICE
CERTIFICATE OF CORRECTION

PATENT NO. : 6,911,438 B2
DATED : June 28, 2005
INVENTOR(S) : Jonathan V. Wright It is certified that error appears in the above-identified patent and that said Letters Patent is hereby corrected as shown below:

Column 4,
Lines 37-51, the following claims should read as follows:
2. A formulation of claim 1, further including an amount of cobalt.
3. A formulation of claim 1, further including an amount of selenium.
4. A formulation of claim 2, further including an amount of selenium.
5. A formulation of claim 4, further including amounts of pyridoxine and folic acid.
6. A formulation of claim 5, wherein the formulation comprises 1000-1125 micrograms of 2-hydroxyestrone; 200-500 micrograms of 17-beta estradiol; 1000-1125 micrograms of estriol; 20 miligrams pyridoxine; 400-800 micrograms of folic acid; 200-300 micrograms of cobalt; and 200-300 micrograms of selenium.

Signed and Sealed this

Thirtieth Day of May, 2006

JON W. DUDAS
*Director of the United States Patent and Trademark Office*